United States Patent [19]

Brar et al.

[11] Patent Number: 4,727,219

[45] Date of Patent: Feb. 23, 1988

[54] GENIC MALE-STERILE MAIZE USING A LINKED MARKER GENE

[75] Inventors: Gurdip S. Brar, Middleton; Oliver Nelson, Cross Plains, both of Wis.

[73] Assignee: AGRACETUS, Middleton, Wis.

[21] Appl. No.: 935,976

[22] Filed: Nov. 28, 1986

[51] Int. Cl.$^4$ .............................................. A01H 1/06
[52] U.S. Cl. .......................................... 800/1; 47/58; 47/DIG. 1
[58] Field of Search .................. 47/58, DIG. 1; 800/1

[56] References Cited

U.S. PATENT DOCUMENTS 4,654,466 3/1987 Lindsey .................................. 800/1

OTHER PUBLICATIONS

Anderson et al., "Hereditary Effects Produced in Maize by Radiations from the Bikini Atomic Bomb I. Studies on Seedlings and Pollen of the Exposed Generation", *Genetics*, 34:639–646, (1949).

Galinat, "Use of Male-Sterile 1 Gene to Eliminate Detasseling in Production of Hybrid Seed of Bicolor Sweet Corn", *Jour. of Heredity*, 66:398-388, (1975).

Galinat, "The Efficiency of the Magasort 6 Machine from Geosource in Separating White and Yellow Kernels Within Inbreds MA-400 and IL-677a", *Maize Genetics Cooperation News Letter*, Mar. 31, 1983, pp. 150–151.

Jones and Mangelsdorf, *The Production of Hybrid Corn Seed Without Detasseling*, Bulletin 55, Conn. Agri. Exp. Station, 1951.

Konzak and Singleton, "The Effects of Thermal-Neutron Radiation on Mutation of Endosperm Loci in Maize", *Proc. Nat. Acad. Sci.*, 42:78–84, (1956).

Konzak and Singleton, "The Mutation of Linked Maize Endosperm Loci Induced by Thermal-Neutron, X-, Gamma, and Ultraviolet Radiation", *Proc. Nat. Acad. Sci.*, 42:239–245, (1956).

Morgan, "Monoploids in *Zea Mays* L. Following Crosses with Untreated and X-Rayed Pollen", (1976).

Smith et al., "Relation Between Mutation Yield and Cell Lethality Over a Wide Range of X-Ray and Fission Neutron Doses in Maize", *Biological Effects of Neutron Iradiation*, Internat. Atomic Energy Agency, 1974.

Stadler, "The Experimental Modification of Heredity in Crop Plants", *Scientific Agriculture*, 9: pp. 557–572, (1931).

*Primary Examiner*—Robert E. Bagwill
*Attorney, Agent, or Firm*—Nicholas J. Seay; Janet E. Hasak

[57] ABSTRACT

A method is disclosed for efficiently using genic male-sterile maize in hybrid seed production which allows economical maintenance of male-sterile stocks. This method enhances a natural linkage between a selected male-sterile gene and a marker gene conditioning an easily observable trait by deletion and screening to create stocks in which the linkage is effectively complete.

26 Claims, No Drawings

4,727,219

GENIC MALE-STERILE MAIZE USING A LINKED MARKER GENE

FIELD OF THE INVENTION

The present invention relates generally to genetic procedures involving maize plants and relates more particularly to procedures intended to develop and utilize male-sterile maize seed for use in hybrid maize production.

BACKGROUND OF THE INVENTION

In current maize, or corn, production in the United States, the vast majority of the seed maize sold to and planted by commercial farmers are single-cross, F1 hybrid varieties. The current commercial techniques for producing hybrid maize varieties require that predictable cross-breedings be achieved between designated male and female parent plants of specific inbred genealogies. Thus the common practice is to plant seeds of the designated male and female lines together in a common field so that pollen from the male parent plants can travel and pollinate the female parent plants.

This procedure is facilitated by the hermaphroditic character of male plants. Each plant has separate male and female inflorescences. Thus either line may be selected as the male or female parent. However because the plants are normally hermaphroditic, in order to ensure that a proper cross is made between the desired male parent and the desired female parent plant, it is necessary to ensure that pollen from the female parent plant does not self-pollinate that same plant or pollinate a sibling female parent plant. In order to ensure that such undesirable self-pollination or sibling-pollination does not occur, the common practice in the hybrid seed maize industry is to physically remove the male inflorescence from the designated female parent plants by detasselling the designated female parent plants by hand. While mechanical devices are presently available to detassel the female parent plants, because of the variability in size of maize plants in any given field and the necessity for not cutting too much of the maize plant away, mechanical processing is not efficient, and thus the detasselling procedure is conventionally done by hand, sometimes in combination with a mechanical device. This process is a very labor-intensive activity and is very concentrated in its time period, normally a time period of four to six weeks in June, July, or August, in the Northern Hemisphere, because the activity must be performed at closely spaced intervals during the flowering period of the maize inbred used as a female parent. This detasselling operation is both a difficult logistical operation, because of the need to acquire large amounts of short-term labor, and is an expensive process because of its labor intensiveness.

Accordingly, much effort has been spent over time to develop maize plants which are male-sterile. The term male-sterile generally designates a plant wherein the male inflorescence on the female parent produces no viable pollen, but the plant still has complete female reproductive capability. The use of a male-sterile maize plant in the hybrid production system avoids the need for detasselling, since the only pollen available for the airborn pollination of the designated female plants, which are male-sterile, is the pollen produced by the designated male parent plant. In this way predictable crosses can be made so that hybrid progeny suitable for field use can be created. Unfortunately, the use of male-sterile maize plants has previously had several inherent disadvantages.

There are two categories of presently known and commercially utilizable systems for maintaining male-sterile stocks of maize plants. One system relies on a so-called cytoplasmic, or non-nuclear, male-sterile trait, and the other system relies on genic, or nuclear chromosomal, trait inheritance to maintain male sterility.

The cytoplasmic male sterility system relies on genes not contained in the nucleus of cells, hence the name. This system is more properly termed cytoplasmic-nuclear, since it depends on both the presence of a cytoplasmic male-sterility gene and the absence of a nuclear restorer gene which can condition restoration of fertility. Since cytoplasmic genetic material is normally transmitted solely from the female parent plant in maize, and is only very rarely, if ever, passed through pollen, the use of a cytoplasmic male-sterile trait in a female parent plant allows pollen to be donated by a male-fertile parent while the resulting progeny plants are reliably male-sterile because of the cytoplasmic gene contribution of the female parent plant. One system disclosed for use of cytoplasmic male sterility to produce commercial hybrid maize seed is disclosed in U.S. Pat. No. 2,753,663.

For a time the United States hybrid seed industry utilized cytoplasmic male-sterile maize lines for the production of hybrid maize seed. The most popular type of cytoplasmic male sterility was referred to as the Texas-Sterile or T-Sterile cytoplasm. This cytoplasmic sterility was used widely in producing several types and varieties of hybrid seed maize for sale until 1970, when there occurred an epiphytotic of a race of T-type *Helminthosporium maydis* causing a form of southern leaf blight in most of the then-existing male-sterile plants and hybrids produced from them. This event convinced many maize breeders that cytoplasmic male-sterility was an inherently inappropriate mechanism for achieving male-sterile plants, since the differences between normal cytoplasm and that carrying male-sterility also seem inherently to affect not only pollen fertility but also disease susceptibility. In addition, the heavy damage caused by this epiphytotic event has created a widespread consumer reluctance to use cytoplasmic male-sterile lines because of fears about reoccurrence of epiphytotic events in the other cytoplasmic male-sterile lines. To date, two other such cytoplasmic male-sterile lines have been identified. Referred to as the C and S types, these types have inherent problems of stability and sterilization of inbred lines, in addition to the consumer and breeder reluctance to use a cytoplasmic male-sterile system. This reluctance, and concerns about epiphytotic events, may be an inevitable consequence of cytoplasmic male-sterility, because the cytoplasmic traits are inherently passed from the female parent in hybrid seed production and therefore the hybrid maize seed produced from a production system using cytoplasmic male-sterile genes must, of necessity, carry the cytoplasmic traits of the male-sterile female parent. In other words, there is no mechanism available using such a system to dominate or mask any undesirable traits carried in this male-sterile cytoplasm, thus ensuring that whatever deficiencies, disease susceptibility, or other traits that are carried in the male-sterile cytoplasm will also be carried in the hybrid seed sold to farmers and the plants resulting from the seed.

The other approach to male-sterility in maize plants is genic male sterility in which the chromosomal nuclear genes of the maize plant cause the male-sterility. Much work has been done on identification of the male-sterile genes in maize, and, to date, at least nineteen different nuclear gene mutations are known which can produce male-sterility. See the list of male-sterile genes, for example, in Column 15 of U.S. Pat. No. 3,861,079. In every presently known inheritable trait which produces male sterility, the sterility is determined by a single gene, and the allele for male-sterility is recessive. The known male-sterile genes have been mapped extensively and the chromosome number and map position of all presently identified genes are well characterized. The possibility of using genic male-sterile lines has long been available to producers of hybrid seed but has not proved sufficiently practical for common use.

The difficulty in the use of conventional genic male-sterile lines arises from the fact that it is difficult to maintain an inbred stock which is homozygous for the recessive allele giving rise to male-sterility. The reason for this is simply that plants carrying the homozygous trait for male-sterility are incapable of producing the pollen necessary to self-pollinate or pollinate siblings also homozygous for the recessive allele. It is, of course, possible to cross-pollinate male-sterile plants homozygous for the male-sterile recessive allele with pollen from male-fertile plants which are heterozygous for the male-sterile gene (i.e. having in their allelic pair one male-fertile allele and one male-sterile allele Ms/ms). The progeny from such a cross-breeding are approximately fifty percent male-sterile and approximately fifty percent male-fertile. Thus, additional homozygous male-sterile plants can be created, but only in a field fifty percent populated by heterozygous male-fertile plants. This system of male-sterility is thus impractical for use in hybrid maize production, since the best that could be expected through the use of such plants is that fifty percent of the designated female parent plants intended for use in the hybrid seed production stage would be male-sterile. Therefore a detasselling operation would be necessary, in any event, to detassel the remaining fifty percent of the plants. Since detasselling is thus necessary in any event in a field utilizing this procedure, there is little commercial advantage in using this process, and it is not widely used at present.

It has been previously noted that certain genes are linked very closely to male-sterile genes. For example, the male-sterile-1(ms$_1$) gene is closely linked for the yellow/white endosperm gene locus. By maintaining stocks of homozygous pollen sterile and white endosperm plants, it is possible to cross these stocks with heterozygous stocks and selecting for male-sterile plants by endosperm color. This procedure is effective, except that the recombinants that do occur will give rise to fertile plants which must be rogued out in the field. The method has not gained widespread use because of the plants produced from these recombinations.

Other more sophisticated systems have been developed to attempt to create genic male-sterile maize plants for use in hybrid seed production. An example of such technique is disclosed in U.S. Pat. No. 3,710,511 and U.S. Pat. No. 3,861,709 to Patterson. That technique utilizes reciprocal translocations and various forms of chromosome deficiencies and duplications to produce male-sterile stocks. This procedure illustrates the complexities envisioned as normally required in creating genic male-sterile maize lines.

One variation of the system of the present invention makes use of one example of a class of genic elements known as transposable elements. Transposable elements, also known as transposons, are genic elements which can spontaneously relocate themselves from one locus to another in a chromosome or to any other chromosome located in the plant genome. Transposable elements were first identified in maize, in the pioneering work of Dr. Barbara McClintock. Several systems of transposable elements have been identified by Dr. McClintock initially, and by others subsequently. Among the systems of transposable elements identified by McClintock is the suppressor-mutator (Spm) system. Spm has a transposition-competent (autonomous) element which encodes the information enabling the excision of the Spm element from one location in the genome and reintegration in another location. The Spm system can affect the expression of the locus into which it is inserted. The Spm system sometimes exhibits an expression phenomenon which has been modeled as a two element system. In modeling the Spm system as a two element system, one element has been referred to as a receptor, Rs and the other element referred to as the suppressor Sp. It has been discovered that the suppressor can be separately located from the receptor and still cause the receptor to repress expression of a gene in which it is inserted. The second component has now been shown to be a defective Spm element in which a portion of the DNA sequence of the Spm has been deleted (Pereira et al., 1985) and which has concomitantly lost the ability to catalyze its own transposition, but which can still be induced to transpose when an intact Spm is present elsewhere in the genome. The second component can be termed a defective Spm (dSpm), or alternatively a receptor factor (Rs), or (I), both definitions describing an inserted and stable genetic factor which suppresses expression of the gene into which it is inserted when the Spm suppressor function is also located in the plant genome.

SUMMARY OF THE INVENTION

The present invention is summarized in that maize plants are produced for use in hybrid seed production, which plants include, in their genome, an allelic pair of recessive genes conditioning male-sterility, and an allelic pair of recessive marker genes conditioning an easily recognized phenotypic trait, the male-sterile genes and the marker genes being on the same chromosome and having a low rate of recombinations between them so that selection of plants for male sterility can be generally made on the basis of expression of the recessive phenotype.

The present invention is also summarized in that the rate of recombination between the male-sterile gene and the marker gene is further minimized by a deletion of chromosomal material between the male-sterile and marker genes to substantially eliminate recombinant events.

It is an object of the present invention to provide a method for producing male-sterile maize seeds through the use of a genic male-sterile trait linked to a recessive marker gene so that the male-sterile seeds or plants can be easily selected from male-fertile plants for maintenance of the male-sterile stock.

It is an object of the present invention to produce and use in the production of hybrid maize seed production genic male-sterile plants which are stable, reliably sterile, and not inherently susceptible to pathogenic activity.

It is another object of the present invention to produce and use male-sterile plants in a breeding system which can be transferred to any desired inbred maize line.

It is an advantage of the present system that the male-sterile trait is passed by recessive chromosomal inheritance and need not be expressed in hybrid seed sold for maize production, even if used in the hybrid seed production process.

Other objects, advantages, and features of the present invention will become apparent from the following detailed description and examples provided hereinafter.

DESCRIPTION OF THE PREFERRED EMBODIMENT

The system described herein is intended to allow plant breeders to reliably reproduce and easily use, both in maintenance stocks and in hybrid seed production, genic male-sterile stocks. The genic male-sterile stocks for the present invention are characterized by a closer than native association between a selected male-sterile locus and a recessive marker gene conditioning an easily observable phenotype. Such a male-sterile stock is maintained by cross-pollination with pollen from a heterozygous stock that carries both a male-fertile allele linked with a dominant marker gene allele and a male-sterile allele linked with a recessive marker gene allele. The progeny of this cross can be selected on the basis of expression of the recessive marker gene phenotype to select for male-sterile plants. Since this method allows for easy and reliable selection of male-sterile plants before sexual maturity, and because the linked male-sterile and marker gene traits can be transferred to any desired inbred line, it becomes feasible to use such a male sterile stock as the female parent in hybrid seed production. Because the male parent in the hybrid seed cross will normally be homozygous for male-fertility and homozygous for the dominant allele of the marker gene, the hybrid seed and the plants produced from it will be male-fertile and have the dominant phenotype of the marker gene, so that any genetic disadvantage which may result from the recessive phenotype will not be carried in the hybrid seed or plants. To optimize the use of this method, much or all of the chromosomal material between the male-sterile gene and the marker gene is deleted to provide a nearly absolute linkage between the two genes.

To begin to create plants in accordance with the present invention, it is first necessary to select an appropriate male-sterile gene locus and an appropriate marker gene. The male-sterile locus can be any male-sterile locus, now known or later identified, as long as the homozygous male-sterile plant is otherwise a reasonably normal healthy plant and as long as, as is now believed to be universally the case, the male-sterile allele is recessive to a male-fertile allele at the locus. Any of the nineteen known male-sterile loci now identified in maize would meet these criteria.

The marker gene is also selected with two objectives in mind. The first objective is that the marker gene should condition a phenotypic trait that is easily identifiable, and is preferably easily identifiable in a seed or in a young plant, and is stable in that its expression is independent of growing conditions. The most desirable marker genes would be those that condition for an easily visible seed trait, such as endosperm color, for reasons that will become apparent. The second criteria is that the marker gene must be selected from genes which are mapped very close to, and are thus naturally linked to some degree to, the selected male sterile locus. Since this process seeks to link the male-sterile gene to the marker gene, the closer the genes are natively on the chromosome, the tighter the native linkage will be. Since this process involves deletion of chromosomal material between the male-sterile locus and the locus of the marker gene, the closer the native marker gene is to that locus, the less material needs to be deleted and therefore the possibility that the deleted chromosomal material would prove to be important to proper growth of the plant would be minimized. Since it is currently hypothesized that only a small fraction of the total chromosomal material of many plants contains seouences identified as having an effect on plant growth, such as coding for proteins, (in maize the figure is believed to be on the order of 5%) the likelihood of significant loss of important growth traits is small for reasonably sized deletions, but clearly the possibility of deleterious effect is minimized if the size of the deletion is also minimized.

The process and product of the present invention envisions the deletion of either most or essentially all chromosomal material between a male-sterile allele and a marker gene allele. This deletion can be created through random mutagenesis and screening. The purpose of the deletion is to eliminate entirely, or at least make extremely rare, recombinant events during sexual reproduction which would separate the recessive marker gene allele from the male-sterile gene allele. In other words, the purpose of deletion is to practically ensure that the male-sterile allele and the marker allele are effectively inseparably bound.

Natively Linked Male-Sterile and Marker Genes

It has been previously proposed to take advantage of the native linkage between a selected male-sterile gene locus and the locus of the recessive marker gene. One example of the selection of a male-sterile locus and an appropriate corresponding marker gene in maize is the $ms_1$ male-sterile locus and the Y gene, conditioning yellow or white seed endosperm color. Both these genes are located on chromosome 6 of the maize and both have been mapped at map unit 17. There is, however, approximately a 0.5% recombinant rate between normal genes at these two loci in maize, thus indicating that there is some additional chromosomal material located between these two loci.

The practice of this prior method using properly selected male-sterile and marker genes can perhaps best be understood through illustration with an example, i.e. with the $ms_1$ and Y gene pair. It is possible, even with no chromosome deletion, to make use of the link between the recessive gene allele y, conditioning white endosperm color, with the recessive $ms_1$ gene allele conditioning male-sterility. Plants homozygous for both recessive alleles would be made sterile and also produce seed with white endosperm if fertilized by pollen carrying the y allele. To maintain this stock, it is crossed to a maintainer stock that is specifically heterozygous with a $MS_1$ allele linked to a Y allele on one chromosome and a $ms_1$ allele linked to a y allele on the other chromosome. The resulting seed (ignoring recombinants temporarily) would be 50% yellow (heterozygous) and 50% white (homozygous). These seeds can be sorted by color to indicate the male-fertility or male-sterility of the plants which may be grown from the seed. Thus the white seeds can be used for maintenance stocks, or for hybrid seed production. For either use, however, there will be plants resulting from recombinant events which separate the linked genes, resulting in some (approximately 0.5%) seeds which have yellow endosperm and are male-sterile or some which are white but male-fertile. While the yellow, male-fertile seeds are not a problem, since they are discarded with the male-fertile seed selected on the basis of endosperm color, the white, male-fertile seeds will result in plants which must be rogued out by hand before pollen is shed. Plants which are male-fertile can be visually or tactilely differentiated from $ms_1$ male-sterile plants, by difference in tassel morphology, prior to pollen shed. Such a roguing procedure may or may not be economically attractive compared to conventional detasselling depending on the rate of recombinations and the skill level of the worker who must do the roguing.

If this method is used for producing male-sterile seed for hybrid seed production, the plants produced by the white seed can be pollinated with pollen from homozygous male-fertile, yellow endosperm, plants so the resulting F1 hybrid seed for sale for maize production would be yellow in color.

Chromosome Deletion Between the Male-Sterile and Marker Gene Loci

It is a desirable advantage in the practice of the process of the present invention that the incidence of recombinations which occur with the above process be reduced or eliminated entirely. This objective is accomplished by a process which involves the deletion of much or all the chromosomal material between the male-sterile gene and the marker gene. The deletion is induced most effectively by random breaks induced by ionizing radiation, and subsequent screening, although some chemical mutagenesis may also produce small deletions. The deletions can be induced using any of several known mutagenesis techniques (although ionizing radiation is the most effective) on seeds or pollen or both of homozygous male-fertile, dominant marker gene lines, since the deletion preferably will involve one or the other, or both of the genes. The plants grown from mutagenized seed are screened for endosperm color and male-fertility. Alternatively, pollen from mutagenized plants can be used to pollinate male-sterile white kernel plants. The resulting seed should be yellow excepting that seeds resulting from mutations will have white endosperm. Similarly all progeny should be male-fertile, but mutant plants would be fully or partially sterile.

Those mutants that show sterility and white endosperm traits should contain deletions of one of the following three types:

(1) Including a portion of the marker gene and extending to an area closely adjacent to the male-sterile locus;

(2) Including a portion of the male-fertile gene and extending to an area closely adjacent to the marker gene; or (3) Including a portion or all of both the male-fertile gene and the marker gene plus all material between them.

Selection among the mutagenized stocks can then initially be made on the basis of the phenotype of the plants produced by the mutagenized seed, since plants of a male-sterile or recessive marker phenotype presumably have a deletion or mutation at the point of interest. Verification of the deletion of a sufficient chromosomal segment requires testing the rate of recombinations between the ms locus and the marker gene locus and testing to ensure that the proper deletion is transmissable through a pollen parent.

Again, using the $MS_1$ and Y system in maize as an example, it is possible to illustrate the advantages in the use of this approach. Assume a stock is created which is ($ms_1^*y/ms_1^*y$), where the asterisk * indicates the deletion. That stock can be maintained easily by crossing to a maintainer line which is heterozygous ($ms_1^*y/Ms_1Y$) to yield progeny 50% white (homozygous) and 50% yellow (heterozygous). Since there is an effectively absolute linkage between the $ms_1$ allele and the y allele, there will be virtually no recombinants and the white seed can be sorted from the yellow seed and used directly for hybrid seed production as the female parent. A homozygous yellow endosperm male-fertile stock would be used as the male parent.

It should be apparent from the foregoing discussion that this method offers a mechanism for reliably using a genic male-sterile trait in hybrid seed maize production. The procedure is reliable and efficient. Since automated optical-mechanical sorting of the seeds is possible based on color, hand labor in the hybrid seed production process can be minimized. Also, since the male-sterile allele and the marker allele, white endosperm color, are both recessive, the heterozygous F1 hybrid seed sold for maize production will display neither phenotype and thus should suffer no deleterious effects from the presence of these recessive alleles.

Again, it is to be understood that other male-sterile loci and marker gene pairs are possible. Another possible pair in maize is the male-sterile-2($ms_2$) locus and the virescent ($v_1$) gene. The recessive virescent $v_1$ gene conditions a seedling which is yellowish-white for several days after emergence from the soil, rather than the normal green. The virescent plant later turns green and matures normally. The $ms_2$ and $v_1$ genes are both located on chromozome 9 at map units 66 and 67, respectively. Again, virescence can be used to indicate, or mark, for male-sterility and, again, the reliability of the linkage can be enhanced by a chromosome deletion between the two loci. Rather than sorting seeds for endosperm color, if virescence is used as the marker, all seeds are planted and half the plants, i.e. the green ones, are uprooted and discarded after emergence. This selection can be done by unskilled labor relatively cheaply. Other male-sterile and marker gene pairs are possible.

Use of Transposable Element with Male-Sterile and Marker Gene Linkage

The variants of the present method described above are perfectly satisfactory for creation of hybrid stocks of any desired inbred line cross, and the marker gene is not expressed in the seed sold for planting. However, some of the yield from the crop grown out from the seed will express the recessive marker allele. For example, again with the endosperm color marker gene in maize, if the seed maize is yellow heterozygous Y/y for endosperm color, the self or sibling pollinated maize crop will be 25% homozygous for the recessive allele of white endosperm color. While this trait is not nutritionally deficient or objectionable, it may be commercially less desirable since maize sold for feed is required by convention in some countries (i.e., the United States) to be predominantly yellow. Thus, it may be desired in some instances to reduce the level of recessive marker allele expression in the seed crop product.

One variant of the process of the present invention to accomplish this objective, which is illustrated here for maize cultivation, involves the use of a transposable element system, here the Spm suppressor-mutator transposable element system, also known as the En, I system. This variant begins with transposition of a defective Spm, lacking the ability to catalyze its own transposition but retaining the capability to suppress gene expression, to the selected male-sterile locus. This transposition is accomplished by allowing random transposition of the defective Spm catalyzed by a transposition-competent Spm, and then selection by appropriate test crossing for insertion of the defective Spm at the proper location. Such a defective Spm, or dSpm, which is transposition-incapable but suppression capable, has also been designated as an Rs or receptor function. A suitable competent Spm system is carried in a maize line designated as bronze-mutable 13. Seeds of bronze-mutable 13 have been deposited with and are available from the American Type Culture Collection, Rockville, Md., ATCC Accession No. 40189.

The desired transposition would result in the insertion of the dSpm in a non-mutant allele at the male-sterile locus. The notation Ms(dSpm) is used here to designate a mutated male-sterile allele, mutated by the presence of the dSpm inserted at the male-sterile locus. The desired mutated male-sterile allele would condition male fertility, unless an active suppressor function (designated Sp) is located elsewhere in the plant genome, in which case it conditions male-sterility. The Sp element can be a transposition-competent Spm system, although is preferably an Spm with its mutator (transposition-inducing) component disabled. Further details about a method for accomplishing this insertion and mutation can be found in U.S. patent application, Ser. No. 756,746 to the inventors here, the disclosure of which is incorporated herein by reference. In this referenced application, the dSpm inserted in the gene locus of interest is referred to as the Rs component.

The creation of a Ms(dSpm) allele allows the efficient use of a male-sterile and marker gene pair with or without the use of a chromosome deletion stock, with less expression of the marker phenotype in the product from the crop production generation. To practice this variation, three stocks are needed, the homozygous male-sterile and marker gene stock, a heterozygous maintainer stock and a stock homozygous for the Ms(Rs) allele. The homozygous male-sterile and recessive marker gene stock is maintained as before, by crossing with the heterozygous maintainer stock, heterozygous for both male-sterility and the marker allele, and selection for the marker gene phenotype in the progeny, e.g. white endosperm color. The maintenance plot will not require roguing for recombinants if a chromosome deletion eliminating recombinants is used. In this variation, both the male-sterile and marker gene stock and the heterozygous maintenance stock should also be homozygous for the Sp function. The presence of the Sp function allows a male-sterile seed increase plot to be constituted by crossing the male-sterile stock to the Ms(dSpm) stock. The male-sterile seed increase plot seed would thus result from the following cross.

$$\frac{ms_1{}^*y\ Sp}{ms_1{}^*y\ Sp} \times \frac{Ms_1(dSpm)Y}{Ms_1(dSpm)Y}$$

The asterisk denotes the deletion or the enhanced deletion or the enhanced chromosome linkage. The male-sterile seed would thus be ($ms_1y/Ms_1(dSpm)Y$; Sp/ ). These would be yellow seeds which would be all male-sterile since the supressor function Sp would cause the mutant male-fertile allele, Ms(dSpm), to also condition male-sterility. These male sterile plants can then be used as the female parent for hybrid seed product with the male parent being any desired inbred line, presumably homozygous for male-fertility and the dominant marker allele. The hybrid seed thus produced would be all fertile and would all condition the dominant marker allele, i.e. yellow endosperm color. From the crop grown on this hybrid, about 6.25% of the maize seed would be homozygous for the recessive allele (i.e. white endosperm color).

EXAMPLES

The following example relates to use of the $ms_1$ locus and y locus coding for yellow (dominant Y) or white (recessive y) endosperm color of the seed. The preferred practice of this invention involves the use of chromosome deletion stocks, so a series of steps were undertaken to create such a stock. The beginning stocks were a male-sterile, white kernel stock ($ms_1/ms_1$, y/y) and a homozygous male-fertile, yellow kernel stock ($Ms_1/Ms_1$, Y/Y) of popular inbred lines W64A and B73.

Seed from the fertile yellow seed stock were irradiated with X-rays in petri dishes at dosages of 5 and 10 KR. Plants were grown out from the irradiated seed and pollen collected. This pollen was then either used as is to pollinate a male-sterile female parent or was alternatively irradiated again, at 1, 1.5 or 2.0 KR, and used to pollinate the female parent male-sterile plants.

A total of 806 such crosses were made. The ears were harvested and scored for endosperm color. Kernels originating from fertilization by pollen which carried deletions at or near the Y locus which render the Y allele non-functional should produce white kernels. Thus several Y locus deletion mutants were directly identified. Several chimeric kernels which had partly white and partly yellow endosperm were also identified.

To identify $Ms_1$ locus deletion mutants, the yellow seed from this cross had to be grown out to plants which could be examined for male fertility. About 11,000 plants were grown out of which 39 had possible deletions or mutations at the $Ms_1$ locus.

To attempt to locate plants having a complete $Ms_1$ to Y deletion, 102 white kernels were planted, grown out, and scored for male fertility. Of these plants, 20 were found to be at least partially sterile. Similarly, the kernels set by the 39 male-sterile plants (identified from plants grown from yellow kernels) when crossed to $ms_1y/Ms_1y$ plants were scored for endosperm color and five additional male-sterile, white embryo genotype (y/y) plants were identified. The endosperm of the kernels from which these plants were grown was yellow. Therefore, this was due to the deletion mutation occurring in the male gamete nucleus which does not condition the endosperm color.

To determine that the white kernel mutants were induced deletions or point mutations at these loci, both in embryo and endosperm, fertile plants obtained from them were selfed and fully or partially male-sterile plants were crossed to Ms₁y/ms₁y stocks. All kernels from this self or cross would be white if the embryos had the same deletion mutation as the endosperm. The kernels resulting from selfing these plants should be all white. In addition, the simultaneous deletion mutation in the white kernel and male-sterile plants were tested by a test-cross with homozygous male-fertile, yellow endosperm plants, selfing the progeny, and separately growing out the yellow and white kernels generated by this cross. For several white kernel male-sterile mutants, all the white kernels from this test crossing regimen produced male sterile plants, thus indicating a successful deletion and a lack of recombinants. However, a larger plant population must be grown to verify the lack of, or the rate of, any recombinations.

In addition, plants obtained from simple "white" (not male-sterile) mutant kernels were crossed as male parent onto msY/msY tester stocks. One-half the test-cross progeny should carry the deletion. The kernels from this test-cross were grown out, plants selfed, and kernels separated into white and yellow and separately planted. For any plant having a deletion at the Y locus sufficient to eliminate recombinations between y and ms₁ loci, the test-cross would yield progeny such that plants from yellow kernels would segregate into fertile and sterile plants at a two to one ratio and all the plants from the white kernels would be fertile. Two such deletions were identified. Three other deletions may have decreased the recombinations between the Ms₁ and y loci.

A similar procedure was followed with the "male-sterile" mutants. These plants were crossed as a female parent to Ms₁y/ms₁y plants. If deletions existed extending into the Y locus, all the kernels from such a cross would be white. Five such plants were identified. For other putative male-sterile plants, to identify deletions that effectively extend to the Y locus, without disrupting it, yellow kernels from the test-cross were grown out, selfed, and the progeny again separated based on yellow or white endosperm. For deletion stocks without recombinations, all the yellow kernel plants would segregate into fertile and male-sterile plants at a two-to-one ratio and all the white kernel plants would again be fertile. Deletion mutants at the Ms₁ locus, Y locus and at both the Ms₁ and Y locus, have been identified which, in small plant populations, show either complete or enhanced linkage of the two genes. The results for Ms₁-y linkage was based on a plant population of 1288 plants and for the ms₁-Y and ms₁-y deletions on 100–400 plants.

Using stocks having the deletion between Y and ms₁ for hybrid seed production is relatively straight forward. The male-sterile, white seed stock is maintained by crossing to a heterozygous maintainer line (ms₁*y/Ms₁Y). The kernels produced are simply sorted by endosperm color to maintain the sterile stock. These linked male-sterile, white endosperm genes can be transferred into any desired genetic background by known crossing and back-crossing techniques. A male-sterile, white endosperm deletion stock can then simply be used as the female parent in hybrid seed production. The seed sold for production would be fertile and yellow. This same stock of deletion mutants can also be combined, as described above, with the Ms₁(dSpm) stocks, if desired, to create hybrid seed that produces a crop lower in white product.

We claim:

1. A method of generating a male-sterile maize stock for hybrid seed production comprising the steps of
   (a) creating a stock of deletion-mutant plants homozygous at a male-sterile locus for male-sterility, homozygous for a recessive easily observable marker gene located closely linked to the male-sterile locus and having a substantial genetic deletion between the male-sterile locus and the marker gene locus;
   (b) crossing the stock of step (a) to a stock heterozygous for the male-sterile allele and for the marker allele;
   (c) selecting from the seed or plants from the cross of step (b) based on expression of the trait conditioned by the marker gene to select and maintain a stock of male-sterile plants.

2. A method as claimed in claim 1 wherein the male-sterile locus is the ms₁ locus and the marker allele is for white endosperm color (y).

3. A method as claimed in claim 1 wherein the male-sterile locus is the ms₂ locus and the marker allele is the virescent (v₁) gene.

4. A method as claimed in claim 1 wherein further the deletion of chromosomal material between the male-sterile locus and the marker gene is complete to avoid recombinations between the two linked genes 5. Maize seed which will, upon growth, yield male-sterile plants, produced by the method of claim 1.

6. A method as claimed in claim 1 wherein the stock of deletion-mutant plants are also homozygous for an Spm system genetic element including the suppressor function (Sp) and wherein the method further includes the step of crossing the homozygous deletion mutant with a male parent stock homozygous for both the dominant marker gene and an insertion mutant male-fertile allele, the mutant male-fertile allele mutated by the insertion therein of a transposition-incapable Spm system which, in the presence of a suppressor function (Sp) elsewhere in the plant genome, will suppress the expression of the male-fertile gene.

7. A method as claimed in claim 1 wherein the deletion-mutant plants are created by mutagenesis and screening of male-fertile plants with the dominant marker allele, and screening for the desired deletion mutants.

8. A method as claimed in claim 7 wherein the mutagenesis is by ionizing radiation.

9. A method for producing male-sterile maize plants for hybrid seed production comprising the steps of
   (a) creating stock of plants which have a male-sterile gene linked to an easily observable recessive marker gene with a minimum of recombinations by random mutation and screening for the linkage;
   (b) crossing plants produced from step (a) which are homozygous for the male-sterility and marker gene linkage with pollen from plants heterozygous for the male-sterility and marker gene linkage; and
   (c) selecting from the seed or plants produced from step (b) for expression of the trait conditioned by the marker gene to select for male-sterile plants for use as the female parent in hybrid seed production.

10. A method as claimed in claim 9 wherein the male-sterile locus is the ms₁ locus and the marker gene is the (y) gene for white endosperm color.

11. A method as claimed in claim 9 wherein the male-sterile locus is the $ms_2$ locus and the marker gene is the virescent ($v_1$) gene.

12. A method as claimed in claim 9 further including, after the step (a), of crossing the plants from step (a) with plants of a desired inbred genetic background, and backcrossing the resulting progeny to plants of that background, to transfer the linked male-sterile and marker gene to the desired genetic background.

13. Maize seed which will, upon cultivation, yield a male-sterile plant, comprising, in its genome, on at least one of an allelic pair of chromosomes, a male-sterile gene linked to an easily observable recessive marker gene, a significant portion of the chromosomal material normally present between the male-sterile locus and the locus of the marker gene being absent so as to minimize recombinations between the male-sterile gene and the marker gene.

14. Maize seed as claimed in claim 13 wherein both of the allelic pair of chromosomes have a deletion of chromosomal material between the male-sterile locus and the locus of the marker gene.

15. Maize seed as claimed in claim 13 wherein sufficient of the chromosomal material between the male-sterile locus and the locus of the marker gene is deleted such that recombinations between the genes effectively do not occur.

16. Maize seed as claimed in claim 13 wherein the allelic chromosome to the chromosome carrying the deletion comprises a mutant male-fertile gene mutated by the insertion of a transposition-incapable Spm system which suppresses the expression of male-fertile gene in the presence of a suppressor function (Sp) of the Spm system elsewhere in the plant genome, and wherein there is further a suppressor function (Sp) of the Spm system elsewhere in the plant genome.

17. Maize seed as claimed in claim 13 wherein the male-sterile gene is the $ms_1$ locus and the marker gene codes for white endosperm color (y).

18. Maize seed as claimed in claim 13 wherein the male-sterile gene is the $ms_2$ locus and the marker gene is the virescent ($v_1$) gene.

19. A method of producing hybrid maize comprising the steps of
(a) maintaining a stock of male-sterile plants both homozygous for male-sterility and homozygous for an easily observable recessive marker gene, in which at least a portion of the native chromosomal material between the two genes is deleted to closely link the two genes, said maintaining occurring by (i) crossing the homozygous plants to a maintainer stock heterozygous for both the male-sterile gene and the marker gene and (ii) selecting among the progeny of the cross by selecting for observation of the trait conditioned by the marker gene to select for homozygous male-sterile, marker gene progeny;
(b) crossing plants of the male sterile stock so maintained with a selected male parent plant homozygous both for male-fertility and the dominant marker gene allele; and
(c) harvesting the seed produced from this cross for use as hybrid seed.

20. A method as claimed in claim 19 wherein the male-sterility gene is at the $ms_1$ locus and the marker gene is for white endosperm color (y).

21. A method as claimed in claim 19 wherein the male-sterility gene is at the $ms_2$ locus and the marker gene is the virescent ($v_1$) gene.

22. A method as claimed in claim 19 wherein the male-sterile gene is closely linked to the marker gene because the chromosomal material between the loci of the two genes present in other maize plants is absent.

23. Hybrid maize seed produced by the method of claim 19.

24. Hybrid maize seed comprising, in its genome, on one chromosome, a male-sterile gene linked to an easily observable recessive marker gene with essentially all of the chromosomal material normally present between the male-sterile gene locus and the marker gene locus being absent.

25. A method of producing hybrid maize comprising the steps of
(a) maintaining a stock of male-sterile plants homozygous for male-sterility at the $ms_1$ locus, homozygous for white endosperm color (y) and homozygous for the suppressor function (Sp) of the Spm system, by (i) crossing the homozygous plants to a maintainer stock heterozygous for both the male-sterile gene and the white/yellow endosperm (Y/y) gene, and (ii) selecting among the progeny of the cross by selection for observation of white endosperm color to select for male-sterile progeny;
(b) crossing plants of the male-sterile plants of step (a) with plants homozygous for yellow endosperm color (Y/Y) and also homozygous for an insertion mutant male-fertile allele mutated by the insertion therein of a transposition-incapable Spm system effective to suppress expression of the male-fertile trait in the presence of a suppressor function (Sp) elsewhere in the plant genome;
(c) harvesting the seed thus produced;
(d) crossing plants produced from the seed of step (c), which should all be male-sterile, with a selected male parent plant homozygous both for male-fertility and yellow endosperm color (Y/Y); and
(d) harvesting the seed produced from this cross for use as hybrid seed.

26. Hybrid maize seed produced from the method of claim 25.

* * * * *